United States Patent [19]

Brown et al.

[11] Patent Number: 4,554,077
[45] Date of Patent: Nov. 19, 1985

[54] METHOD AND APPARATUS FOR MONITORING SEWAGE TREATMENT EFFICIENCY AND DETERMINING SEWAGE SOURCES

[75] Inventors: Leslie Brown; James Braven; Michael M. Rhead, all of Plymouth, England

[73] Assignee: Devon County Council, England; a part interest

[21] Appl. No.: 528,105

[22] Filed: Aug. 31, 1983

[30] Foreign Application Priority Data

Jul. 1, 1983 [GB] United Kingdom ................. 8317933

[51] Int. Cl.⁴ ............................................. C02C 1/00
[52] U.S. Cl. .................................... 210/656; 210/746; 210/96.1; 210/198.2; 210/908; 436/56; 436/161
[58] Field of Search ................ 210/656, 659, 745, 746, 210/94, 85, 96.1, 198.2, 143, 905, 908, 909; 436/27, 56, 161

[56] References Cited

U.S. PATENT DOCUMENTS

| | | | |
|---|---|---|---|
| 2,046,365 | 7/1936 | Cassidy et al. | 436/56 |
| 3,180,142 | 4/1965 | Bombardieri | 436/27 |
| 3,372,746 | 3/1968 | Sanderson et al. | 436/27 |
| 4,235,716 | 11/1980 | Halpaap et al. | 210/656 |
| 4,252,537 | 2/1981 | Cattran et al. | 210/656 |
| 4,333,838 | 6/1982 | Ballnus | 210/745 |

FOREIGN PATENT DOCUMENTS

| | | | |
|---|---|---|---|
| 0594807 | 3/1960 | Canada | 436/27 |
| 0108754 | 7/1982 | Japan | 436/161 |

OTHER PUBLICATIONS

Large Bore Coated Columns in Analysis for Trace Organic Pollutants in Water by Hussein et al. in Journal of Chromatography 243 (1982) 43–50.

Liquid Chromatography Catalog of Rainin Instrument Co., Inc. p. 108, published 1982.

Identification and Estimation of Neutral Organic Contaminants in Potable Water by Burnham et al. in Analytical Chemistry, vol. 44, No. 1, Jan. 1972, pp. 139–142.

Langes Handbook of Chemistry, 10th ed., 1961 pp. 955–960.

Primary Examiner—John Adee
Attorney, Agent, or Firm—Cushman, Darby & Cushman

[57] ABSTRACT

A method of tracing sewage effluent is described in which samples of fluid flows are subjected to high performance liquid chromatography with respective elution systems capable of eluting different selected compounds therefrom, and the concentration of each compound in the sample is determined spectroscopically. The method is used to determine sewage flow paths in natural water bodies, such as rivers, to check for contamination by sewage, to determine possible sewage sources, the detection of uric acid, for example, being indicative of a human source; and to monitor the effluent from sewage treatment plants.

A monitoring system for sewage treatment works is also described in which bromophenol blue is added to the sewage influent to the biodegradation stage as a dilution indicator and the changes in the bromophenol blue concentration and in the concentration of a biodegradable sewage component, such as uric acid, are monitored throughout the stage to give an indication of the progress of the biodegradation reaction; this information is used in controlling the operation of the plant to maximize its efficiency.

20 Claims, 18 Drawing Figures

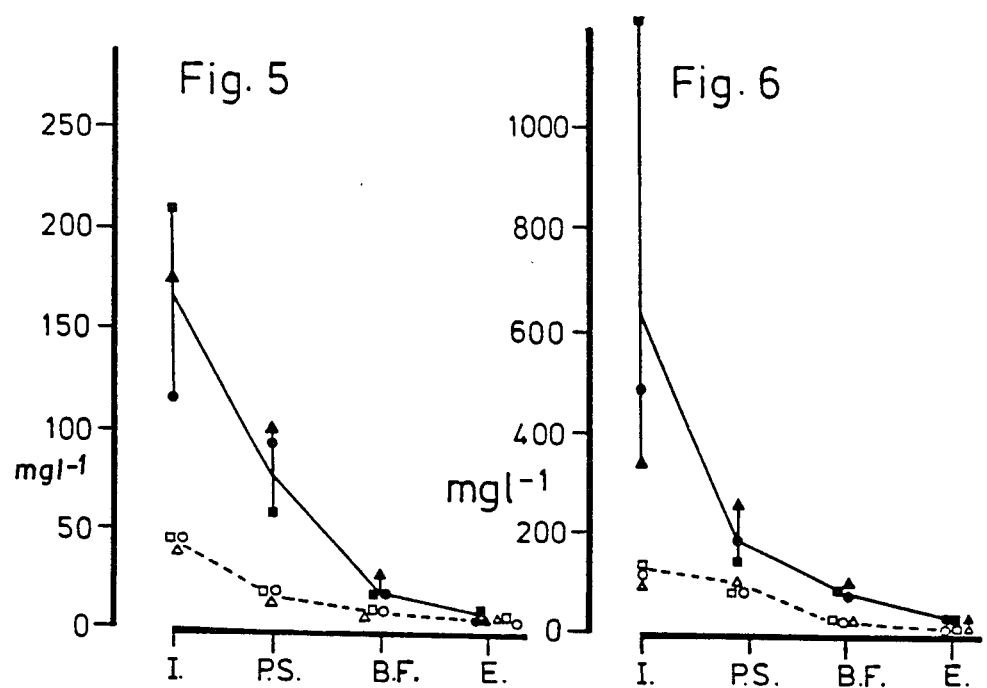
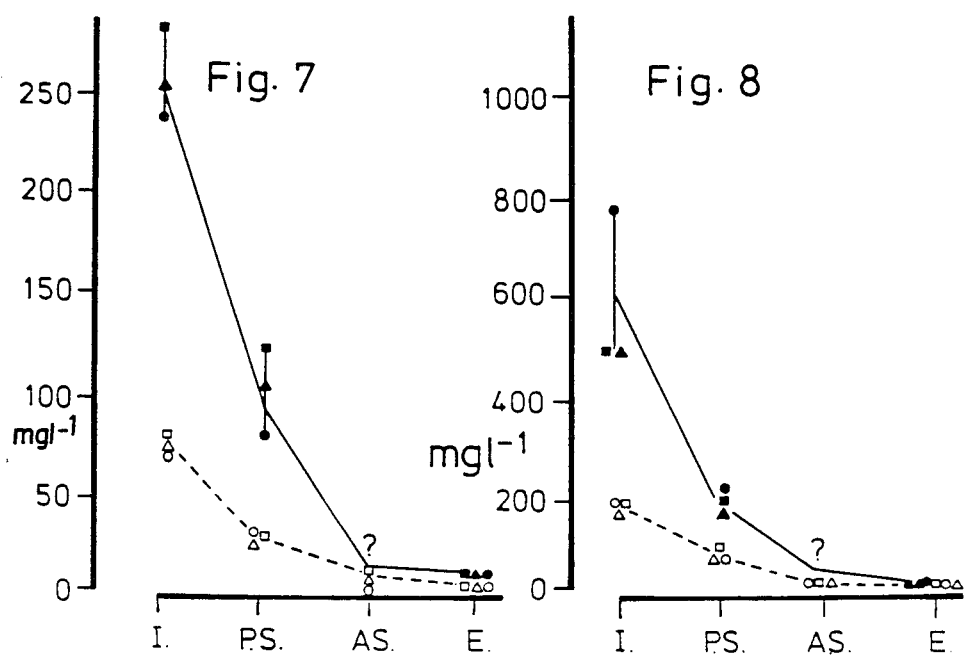

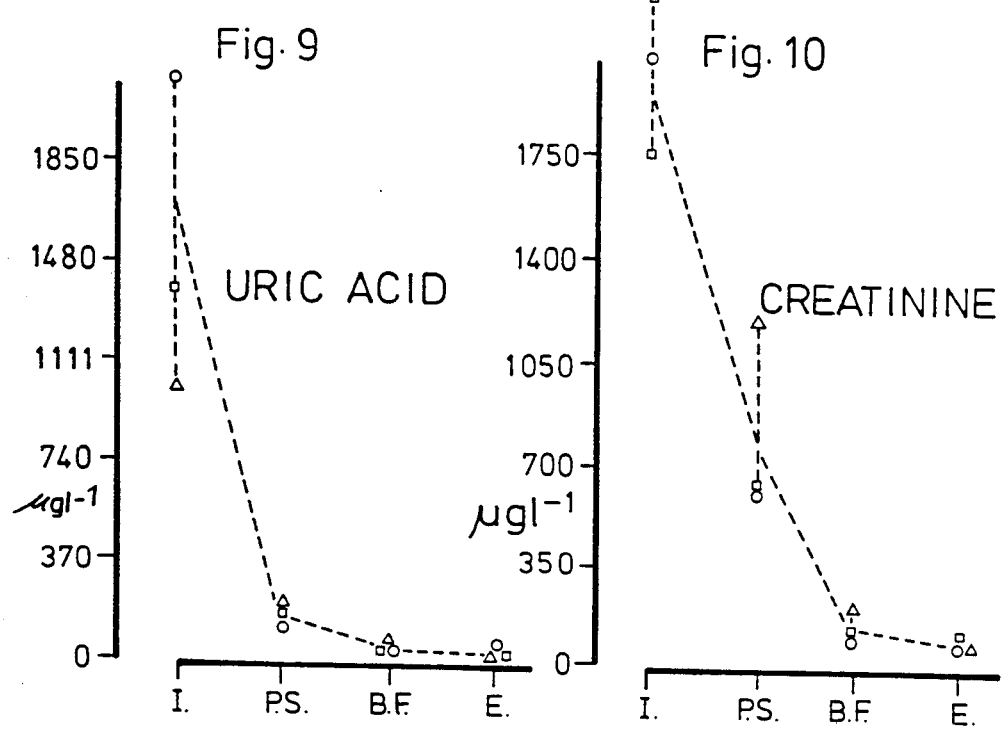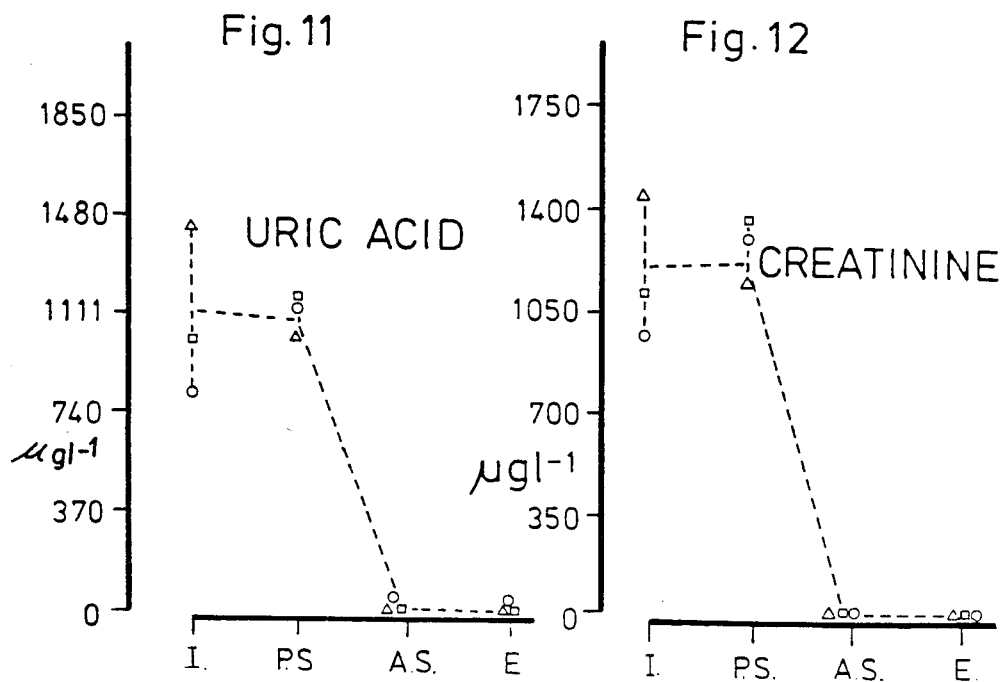

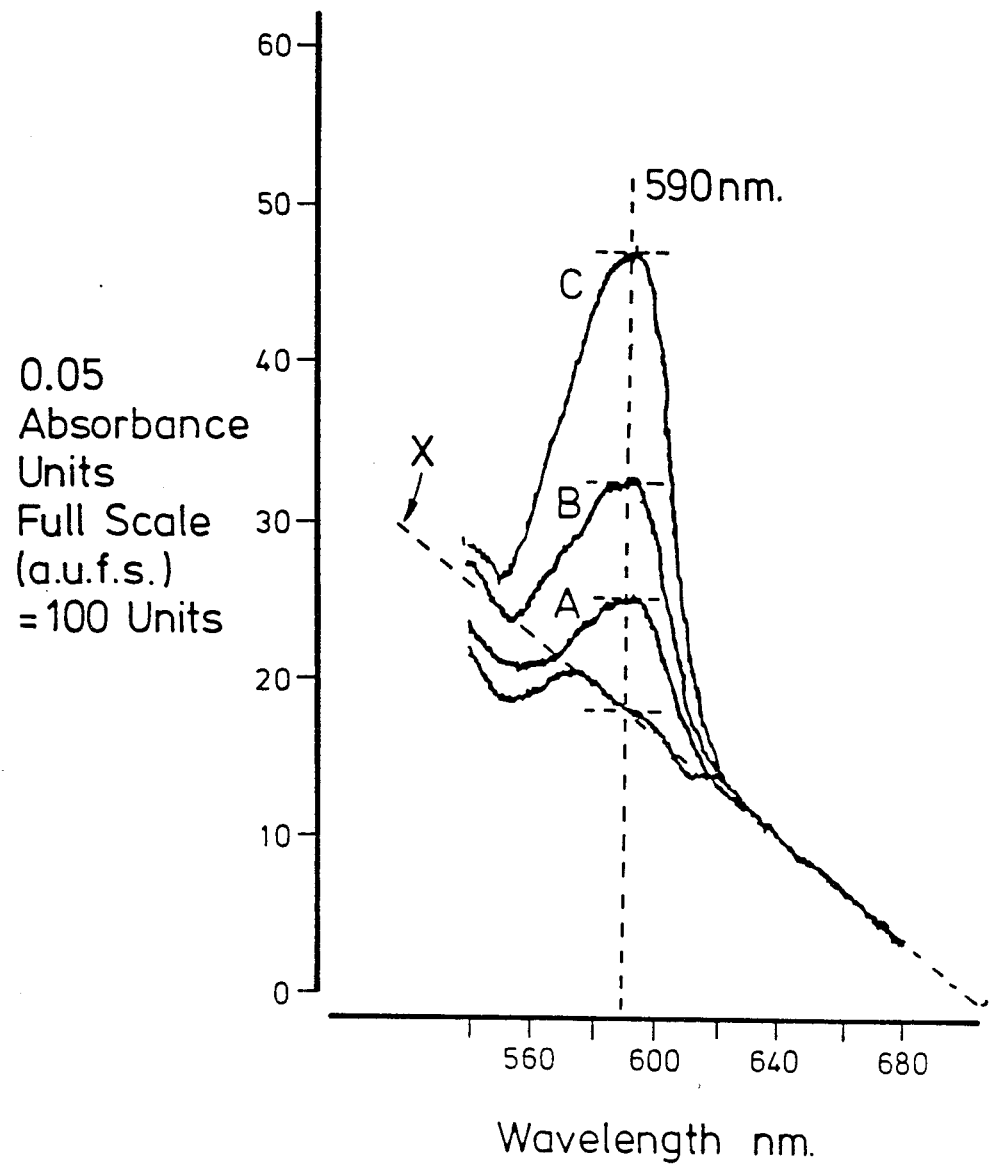

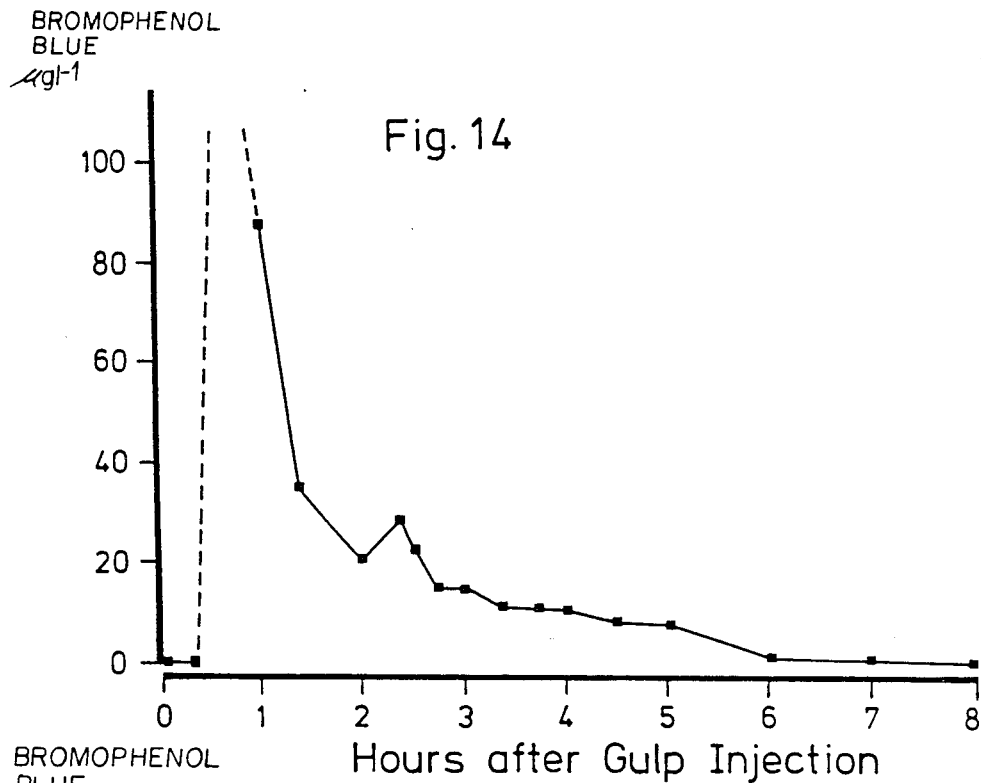
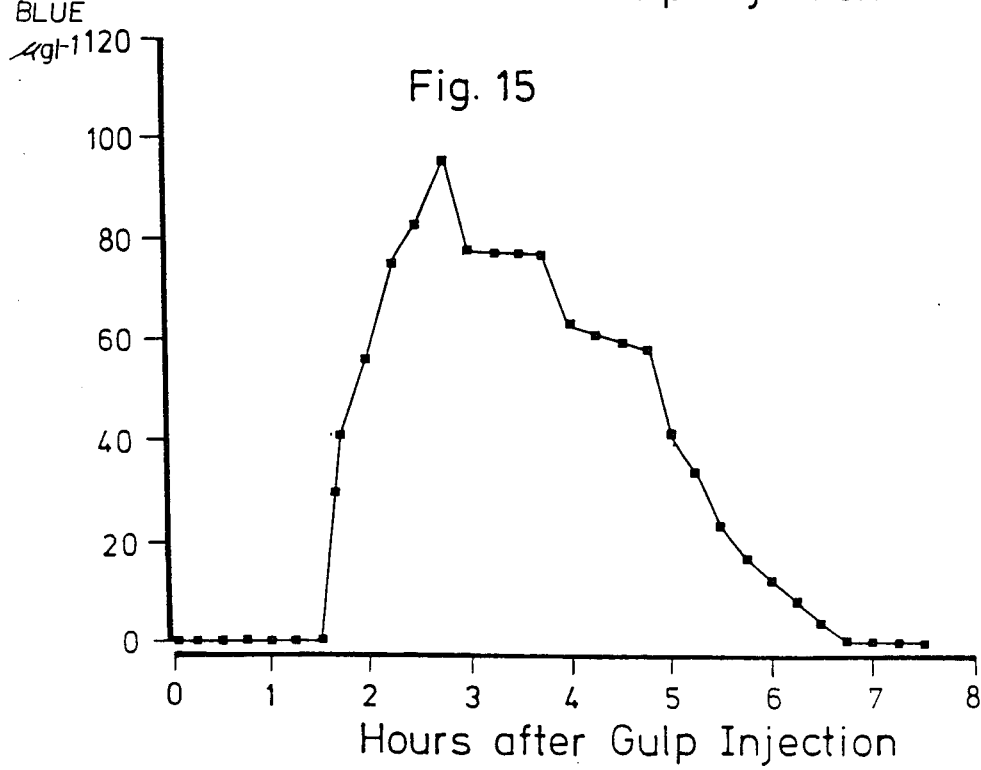

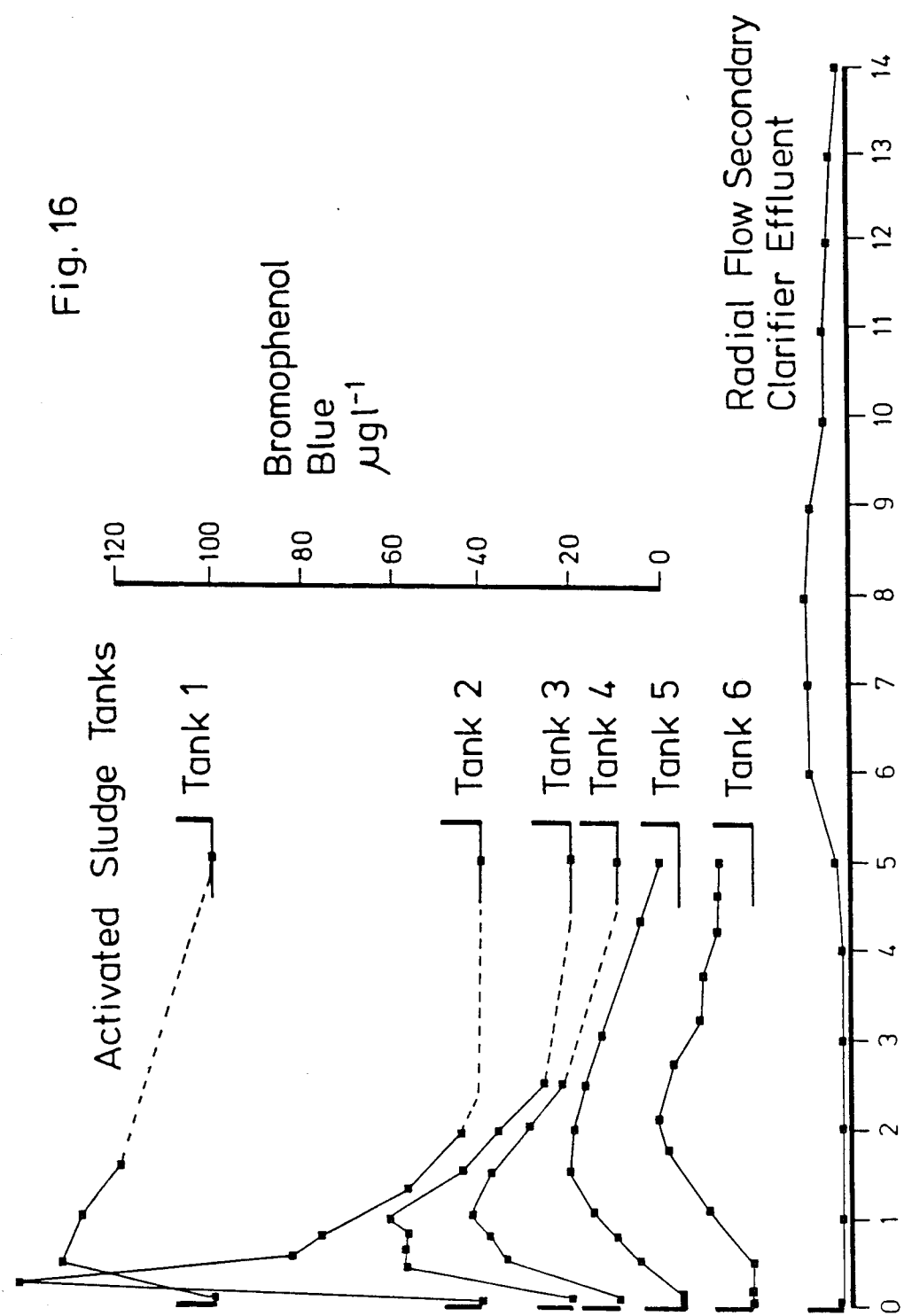

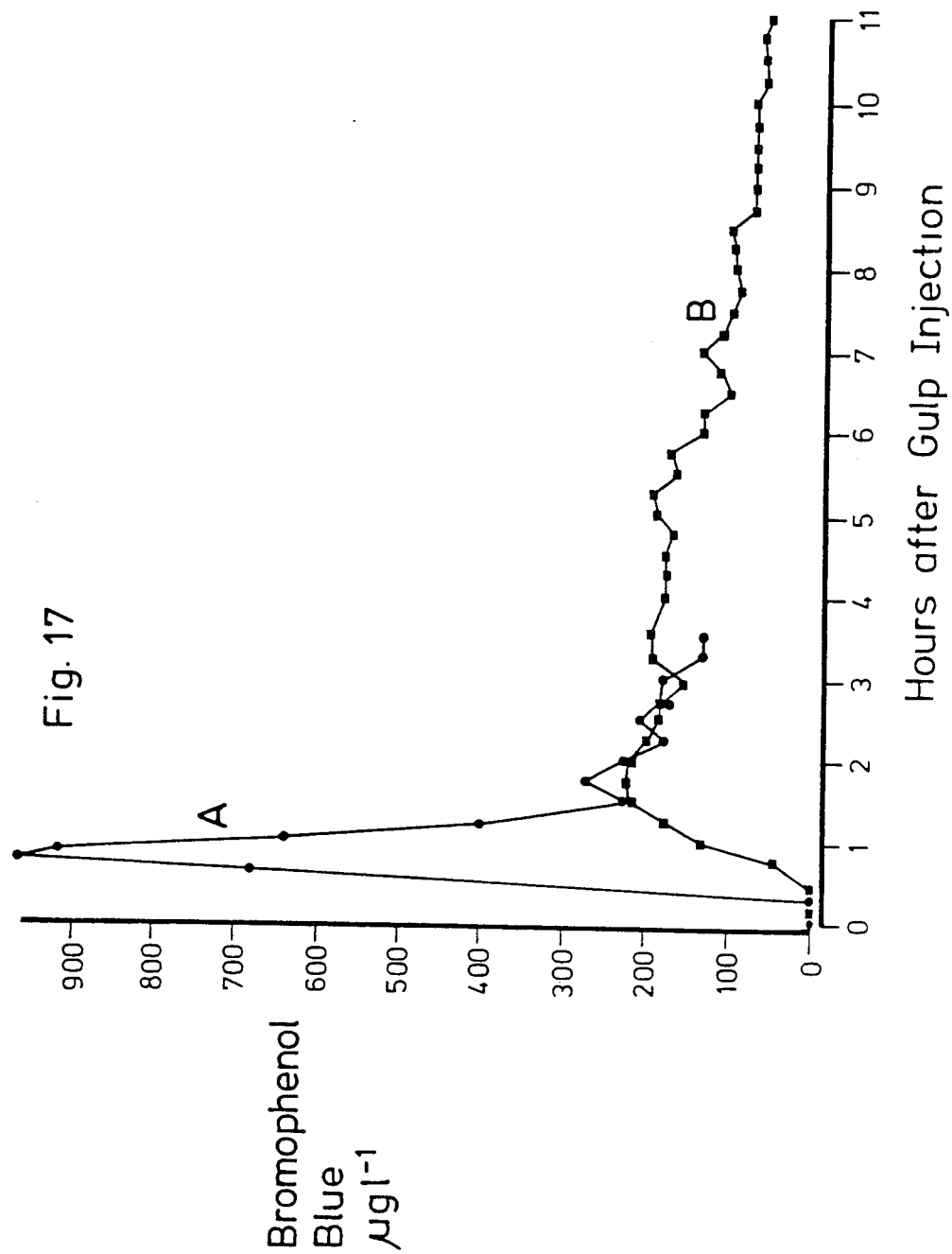

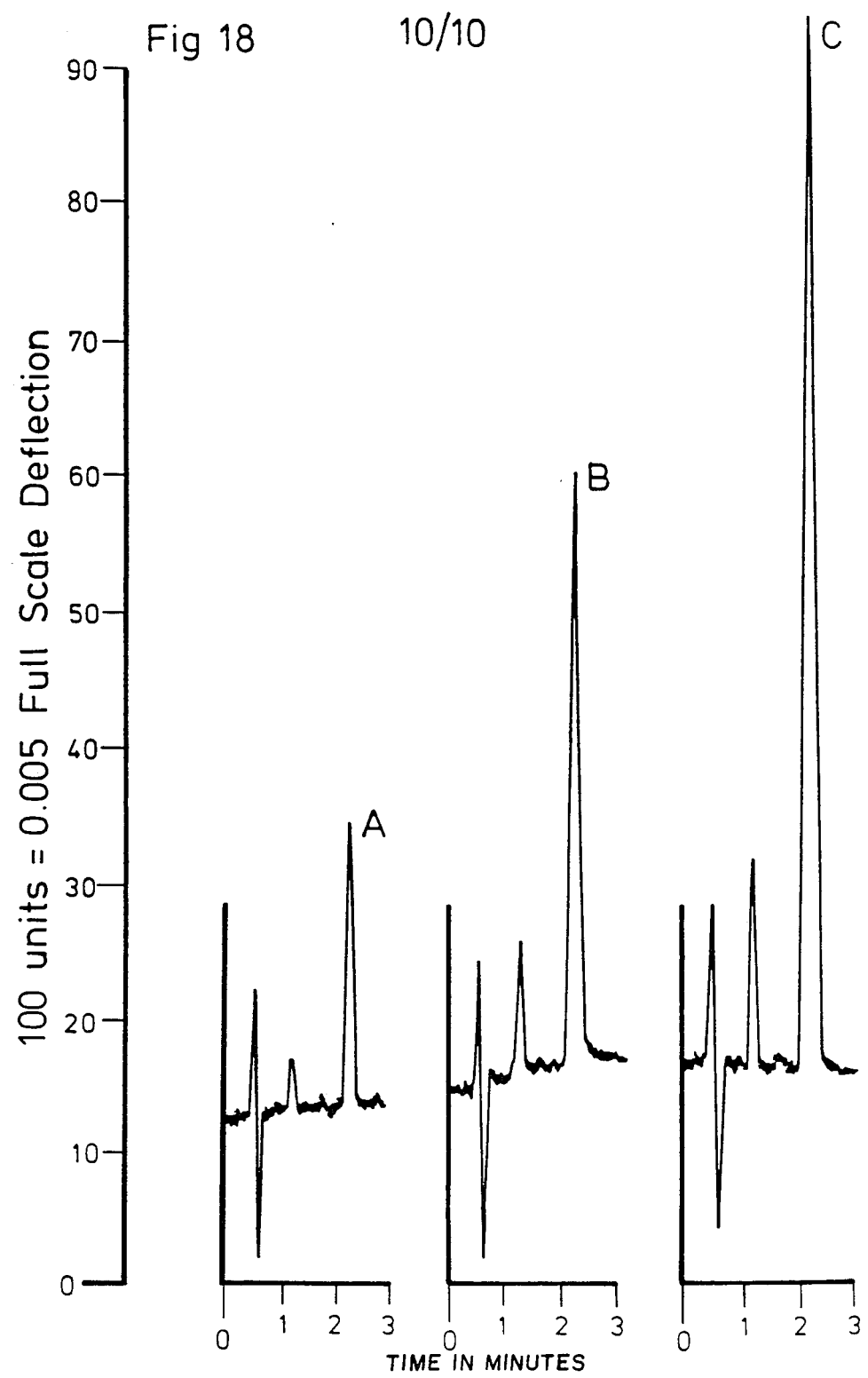

METHOD AND APPARATUS FOR MONITORING SEWAGE TREATMENT EFFICIENCY AND DETERMINING SEWAGE SOURCES

BACKGROUND OF THE INVENTION

The present invention relates to the qualitative and quantitative tracing of sewage flows and to the monitoring of reactions in fluids, with particular reference to biodegradation reactions in sewage treatment plants, to the monitoring of the operational efficiency of such plants and to the control thereof.

The need to trace sewage effluents in environmental water bodies, such as rivers, estuaries and coastal waters is self-evident but at present various difficulties are encountered in putting it into effect. For example colored tracers, which may be added to a flow to give rapid preliminary information on flow paths in non-turbid flows, are generally adsorbed on to solids suspended in sewage flows and hence give anomalous results, if any, under these conditions. Constituents of the sewage itself, such as potassium and sodium chlorides, although more difficult to assess than coloured tracers, are usable in fresh water conditions but, naturally, cannot be used as tracers in salt waters. Many other sewage constituents, such as urea, also occur naturally at levels similar to those found in sewage or have until now been very difficult or time-consuming to estimate.

One object of the invention is, therefore, to provide a more convenient method of tracing sewage flows than is currently available.

A further requirement in connection with sewage effluents is that of monitoring the outflows from sewage-treatment plants to ensure that the quantities of remaining pollutants are below statutory maximum levels.

At present two types of large-scale sewage-treatment plant are in widespread use and are known as activated sludge plants and biological filter plants respectively. In general terms, these plants include a primary treatment stage in which suspended solid particles are separated from liquid sewage and a secondary treatment stage in which the liquid is subjected to biodegradation to render it fit for discharge into the environment after a secondary filtration process for removing further suspended matter.

The operational efficiency of such plants is currently determined by BOD (biological oxygen demand) and COD (chemical oxygen demand) analyses on the effluent discharged, maximum allowable BOD and COD values being laid down for each plant according to the size and nature of the water body receiving the discharge.

Such BOD and COD values, however, are a combination of a large number of factors, requiring complex and time-consuming measurements, and a need has been felt for a simple method of obtaining reliable information on the basic processes at work in a sewage plant and on the operational efficiency of the plant.

After considerable research, it has been found possible to detect a selected sewage component by a simple reliable method which can be adapted for use in tracing sewage flows and it has also been found that the estimation of a single sewage component may be used in the monitoring of the operational efficiency of a sewage-treatment plant.

SUMMARY OF THE INVENTION

One aspect of the invention accordingly provides a method of tracing sewage effluent in a water body, including the steps of:
 sampling said water body;
 filtering the sample taken;
 eluting a portion of said filtered sample by high performance liquid chromatography with an elution system capable of separating a selected sewage component from said portion; and
 testing the eluent after chromatography for the presence of said selected component.

The selected sewage component is preferably a simple organic molecular which does not occur naturally at comparable levels to those occuring in sewage: such compounds are, for example, uric acid, creatinine and hippuric acid. Filtering is carried out to separate solid matter which could block the chromatographic apparatus and also bacteria which could degrade the organic compound and reduce its concentration in the sample; the analysis should, in any case, be effected within 24 hours of sampling.

A particular advantage of the present method is the rapidity with which it can be carried out: for high performance liquid chromatography (HPLC), only a small sample (10–1,000 $\mu$l) is required, which immediately reduces the filtering time compared with known methods, and the chromatography itself may be carried out in a matter of minutes. The presence of the selected compound is preferably detected by a spectrophotometric method which not only gives a rapid qualitative answer as to whether or not the compound is present in the sample but can also be arranged to give a quantitative result. It will be appreciated, however, that alternative methods of detection, such as electrochemical methods, could alternatively be used to give accurate quantitative results. Such concentration measurements may be used to estimate the degree of mixing of a sewage flow with a water body, such as a river, into which it is discharged. For such estimations the degradation of the selected organic compound would also have to be taken into consideration at points remote from sewage sources.

A further advantage of the present method is that extremely low concentrations, of the order of 1–10,000 $\mu g l^{-1}$, of the selected compound can be detected.

A specific use of the method of the invention is in the determination of the presence, and possible sources, of pollution in a water body. As an example, the presence of uric acid in a sample would indicate pollution by humans since we are the major source of this compound in the environment, the few birds and reptiles which also excrete it only producing small quantities in comparison. The presence of uric acid may thus also indicate the possible presence of human pathogens, such as typhoid or cholera bacteria in a water source.

The present method also lends itself to the rapid assessment of several compounds in a sewage sample since the same chromatographic apparatus may be used, for all the determinations, only the elution system being changed according to the compound to be detected. The detection of the relative proportions of several compounds in a sample may be used to give further information on the source or sources of the sewage. For example, it has been found that human excrement contains a fairly well-defined ratio of uric acid to hippuric acid; if a sewage sample is found to contain these compounds substantially in these proportions then it can be said to be from a largely human source. A larger proportion of hippuric acid than in human effluent could, however, indicate farm livestock as a possible major source of the sewage; such indications would of course be cross-checked with other environmental studies at or near the sampling points.

The above uses of the method of the invention relate generally to the detection of sewage in the environment but, as mentioned in the introduction, the invention is also concerned with the monitoring of sewage in treatment plants. Accordingly the invention also provides a method of monitoring the operational efficiency of a sewage treatment plant having a biodegradation stage, including the steps of:

sampling the flow through said plant at least after its outlet from said biodegradation stage;

filtering each sample taken, and analyzing each filtered sample to give information relative to the concentration of a selected, biodegradable compound in the respective sample.

The above method results from research which has demonstrated that the concentration of a single biodegradable compound, such as uric acid, in sewage effluent can indicate the overall level of pollution in the effluent for checking against the statutory levels allowable. The selected compound is preferably estimated by the HPLC method combined with spectrophotometric analysis, as outlined above. The biodegradable compound may be an additive to the sewage but is preferably a component of the sewage itself and samples are preferably taken at several points in the biodegradation stage as well as at its outlet.

The above method enables the effluent from a sewage treatment plant to be monitored routinely to provide a rapid test of whether or not a plant is operating properly to reduce the pollution of the effluent discharged below the statutory maximum value, but concentration measurements of the biodegradable compound alone cannot, in themselves, give a complete picture of the biodegradation process since the sewage flow is mixed with additional liquid in the secondary treatment stage; the uric concentration is thus reduced both by dilution and by biodegradation.

In order to investigate the progress of the secondary treatment more fully, it is necessary to trace the fluid flows within a sewage treatment plant both qualitatively and quantitatively, and preferably on a routine basis. For this purpose the invention may further include the steps of:

adding a measured quantity of a tracer which is inert to the reaction conditions in the biodegradation stage and which is not adsorbed by solid matter in said stage to said flow prior to said inlet to said biodegradation stage;

determining information relative to the concentration of said tracer in each said sample taken, and determining, from said information relative to the concentration of said tracer in each said sample together with said information relative to the concentration of said selected, biodegradable compound in each said sample, information relating to the proportion of said selected biodegradable compound in the flow at the inlet to the biodegradation stage which has been biodegraded at said at least one point within said biodegradation stage and at the outlet from said biodegradation stage.

The tracer may be a radioisotope since these have been used successfully in flow studies on sewage plants but their use involves a number of disadvantages, particularly with regard to routine monitoring. In the first place prior authorization is required for their use in many countries: this may take several months to arrange for individual studies and is unlikely to be granted for routine tests since these would involve the discharge of unacceptably large quantities of radioactive material into the environment. Secondly, radioisotopes must be handled by qualified personnel and the expense of training sufficient technicians, combined with costs of producing and transporting the isotopes themselves would be prohibitive for routine use.

A more convenient method of tracing fluid flows in general, in that it is not bound by the restrictions applied to radioisotopes, involves the use of colored tracers but as mentioned above, a difficulty here is that colored tracers at present in use are adsorbed on to particles present in sewage plants and are removed from the liquid phase and/or are attacked by the chemical or bioloigical processes active within the plants. Other tracers, such as salts (e.g. lithium chloride) which are unreactive and not adsorbed are much more difficult and time-consuming to evaluate than colored tracers and have the basic disadvantage of being colorless so that they cannot be used for simple, initial tests on flow paths by visual inspection. Considerable research has therefore been carried out into alternative tracers and surprisingly, it has now been found that bromophenol blue, a compound which has been used up till now as a pH indicator, that is, for its ability to change color, is usable as a tracer, particularly in its ionized form, above pH4, in which it displays an intense blue coloration. More particularly it has been found that bromophenol blue is usable as a tracer in sewage treatment plants since tests have shown that, above pH4, bromophenol blue is not adsorbed to any substantial extent on solid sewage and other particulate matter present in such plants, nor does it react with chemicals, such as flocculents, which may be used as part of the treatment, nor is it degraded by the bacteria which cause biodegradation of sewage. A further important characteristic is that it is not toxic, at least in the concentrations needed for flow tests in sewage plants.

The general use of bromophenol blue as a tracer is described more fully and claimed in our copending patent application U.S. Ser. No. 528,104 of even date herewith but is also given, by way of explanation, in the detailed description below, with reference to the accompanying drawings.

In the present context, bromophenol blue is the preferred tracer for evaluating the dilution of the sewage flow in the biodegradation stage of a sewage-treatment plant and although information on its concentration in the samples may be determined by any suitable method, for convenience, it is preferably determined by the same method as that used for the biodegradable compound.

The sampling and filtering may be carried out manually but is preferably automatic, the automatic samplers supplying the analytical apparatus directly. The analysis results may be provided in any convenient form for use by a plant operator in checking for malfunctions in the plant or for determining at what point in the biodegradation stage the sewage has been degraded sufficiently for it to be discharged safely to the environment. Passage through subsequent parts of the stage will thus be needlessly wasteful of power and materials.

The use of the H.P.L.C. and spectrophotometric method of analysis described above enables an indication of the degradation efficiency of the plant to be obtained within minutes of sampling. On checking the analysis results a plant operator may shut down any parts of the treatment stage which are excess to requirements, reducing the operating costs, or may open additional stages as needed, thus improving the overall operating efficiency of the plant.

Although the plant personnel may themselves effect any necessary calculations and comparisons on the data supplied by the analysis apparatus, this data may be fed to comparator means arranged to provide a read-out directly related to the operating efficiency of the sewage plant for use by the personnel. Alternatively data may be fed to a computer arranged to control the operation of the plant directly to maximize its operating efficiency.

Although it is particularly useful to monitor the secondary, biodegradation stage of a sewage treatment plant, the entire system is preferably monitored through autosamplers located, for example, at the inlets to and outlets from each processing stage in the plant.

According to a further aspect of the invention there is provided a monitoring system for the biodegradation stage of a sewage-treatment plant including:

means for metering a tracer which is inert to the reaction conditions in said biodegradation stage and which is not adsorbed by solid matter in said stage into the sewage influent to the biodegradation stage;

respective automatic sampling means for sampling at least said influent and the effluent from said biodegradation stage; and analyser means arranged to effect two determinations on each of the samples taken by said respective automatic sampling means, one of said two determinations being related to the concentration of a selected, soluble biodegradable sewage constituent in said sample and the other of said two determinations being related to the concentration of said tracer in said sample.

A sewage treatment plant provided with a monitoring system as described above preferably further includes comparator means arranged to receive all said determinations effected by said analyser means and to process them to provide an indication of the operating efficiency of the degradation stage.

The method and apparatus described above have been developed with sewage treatment monitoring in mind but it will be appreciated that the invention has much wider applications. Indeed, a broader aspect of the invention provides a method of monitoring a reaction in a continuous flow system including the steps of:

simultaneously sampling a fluid flow containing a reactant and a tracer inert to the reaction conditions at its inlet to a reaction zone and at at least one point selected from points within said reaction zone and a point at the outlet from said zone;

subjecting two portions of each sample taken to high performance liquid chromatography, one of said two portions being eluted with an elution system capable of separating said reactant therefrom, and the other of said portions being eluted with an elution system capable of separating said tracer therefrom;

analyzing said elution systems after said chromatography to give information relative to the concentration of said reactant and said tracer in each said sample; and determining from said information the proportion of said reactant entering the reaction zone which has reacted at said at least one point.

BRIEF DESCRIPTION OF THE DRAWINGS

The invention will be more particularly described, by way of example, with reference to the accompanying drawings in which:

FIGS. 5 and 6 are graphs showing the results of BOD and COD assessments respectively at various points in the sewage treatment plant of FIG. 3; and FIGS. 7 and 8 are graphs showing the results of BOD and COD assessments respectively at various points in the sewage treatment plant of FIG. 4;

FIGS. 9 and 10 are degradation profiles of uric acid and creatinine respectively in the plant of FIG. 3, and FIGS. 11 and 12 are degradation profiles of uric acid and creatinine respectively in the plant of FIG. 4, FIG. 13 is a graph showing the results of the spectroscopic analysis of bromophenol blue solutions at different concentrations;

FIG. 14 is a graph showing variations in bromophenol blue concentration with time at the outlet from the vertical-flow primary settlment tanks forming part of the plant of FIG. 4;

FIG. 15 is a graph similar to FIG. 14 showing results after flushing of the inlet manifold to the tanks;

FIG. 16 shows graphically the variation of bromophenol blue concentration with time in each of the activated sludge tanks and at the outlet from the radial-flow secondary clarifiers of the plant of FIG. 4;

FIG. 17 shows graphically the variation of bromophenol blue concentrations with time at the central collection core of the biological filter and in the effluent from the secondary clarifier in the plant of FIG. 3;

FIG. 18 is a graph showing the results of the spectroscopic analysis of bromophenol blue at different concentrations after elution by high-performance liquid chromatography.

DESCRIPTION OF THE PREFERRED EMBODIMENTS

Tracing of sewage discharges

Figure 1:
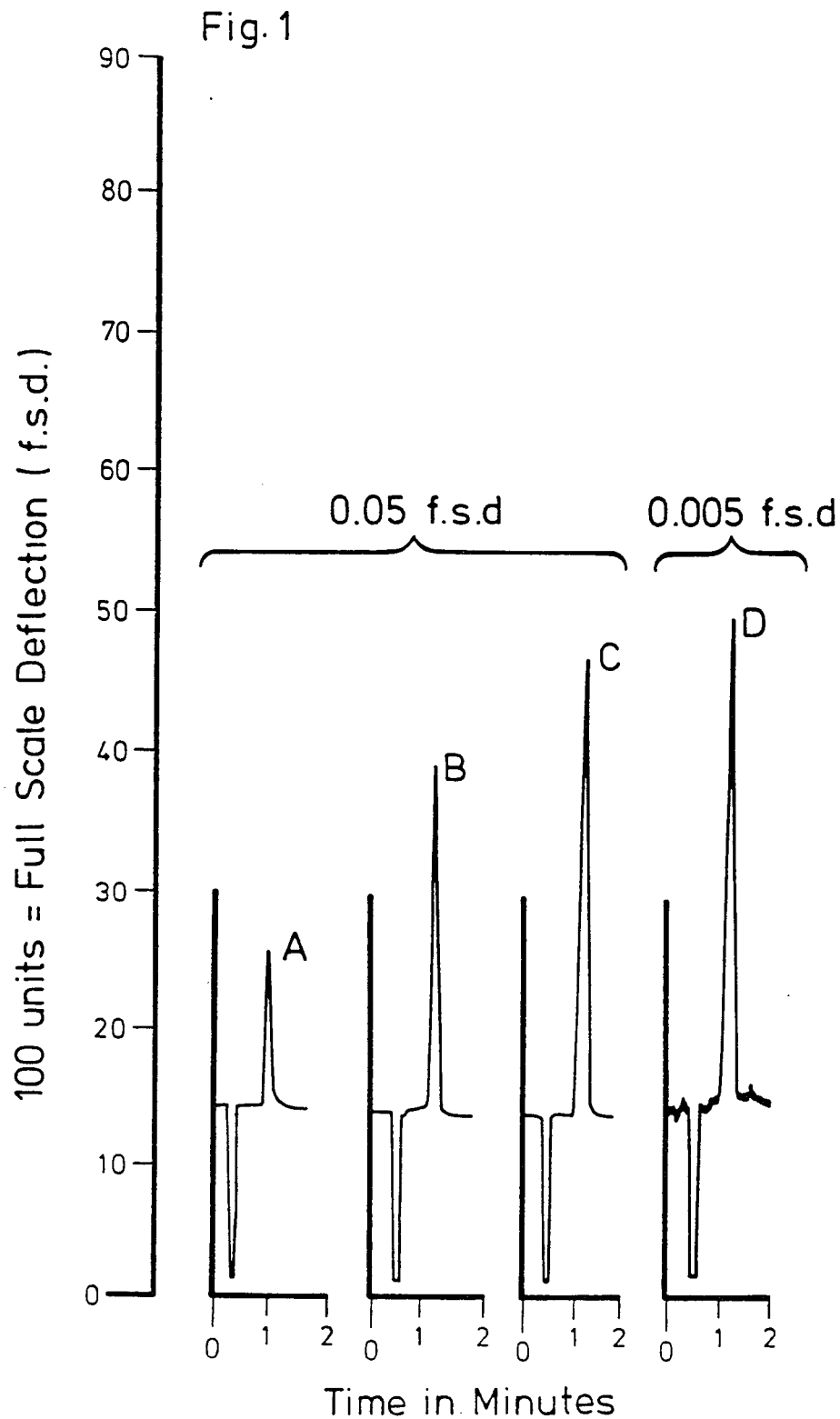
FIGS. 1 and 2 are chromatograms showing the results of the spectroscopic analyses of uric acid and creatinine solutions respectively at different concentrations after elution by high-performance liquid chromatography.

Water samples were taken from various points in a river estuary and catchment area into which sewage was being discharged and the samples were tested for their contents of uric acid (urate) and creatinine as follows.

The water samples were filtered immediately after collection through a 0.45 $\mu$m filter using a Millipore Swinnex apparatus (0.25 cm) to remove microbes and prevent biodegradation of the uric acid and creatinine continuing in the samples; the first 30 ml of filtrate were discarded. Analsyis was carried out as soon as possible thereafter and at least within 24 hours of sampling, the samples being stored in the meantime at 4° C. in the dark to prevent significant changes in the uric acid and creatinine concentrations.

The analyses were effected by a high performance liquid chromatographic (HPLC) method a 100 μl aliquot of each filtered sample being injected on to a Hypersil 5 μm octadecasilane column (stainless steel—100×4.6 mm) operated with a flow rate of the isocratic elution system of 2 ml min$^{-1}$ and a pressure of 880 psi. Detection was effected by a U.V. detector, the results being recorded by a Houston omniscribe recorder operated at a sensitivity of 0.05 or 0.005 f.s.d. (full scale deflection=100 units).

The elution system was varied according to the compound to be detected: for uric acid the system was 0.02% v/v orthophosphoric acid in distilled water and for creatinine, 0.01M sodium dihydrogen phosphate titrated to pH7.5 with 0.01M disodium hydrogen phosphate. The detection wavelength for uric acid was 280 nm and for creatinine was 230 nm.

Figure 2:
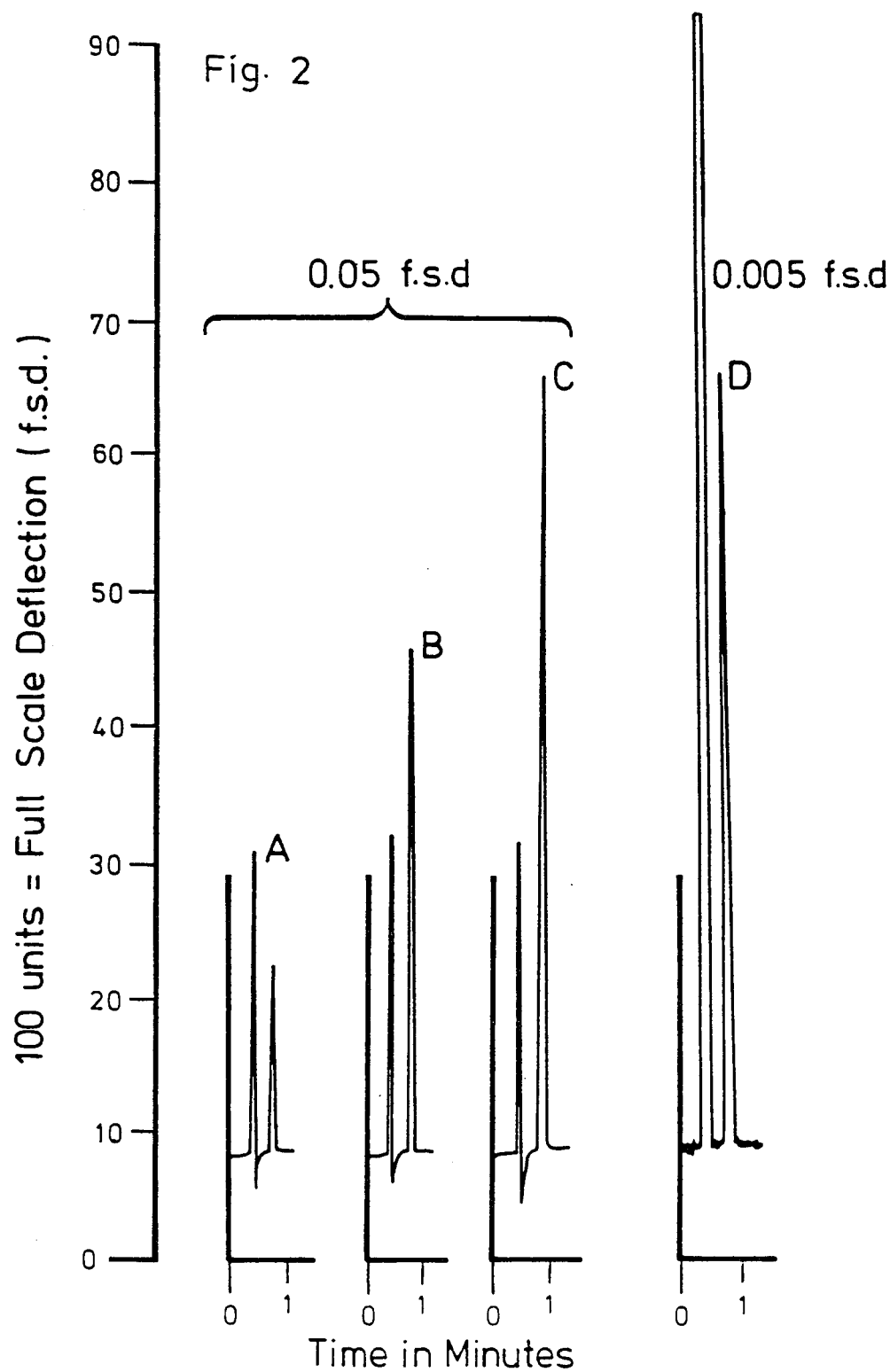

The required concentrations were calculated by comparing the record for each sample with standard recordings made with the same apparatus operated under the same conditions. Results for the standard solutions given in the table below are shown in FIG. 1 (uric acid) and in FIG. 2 (creatinine).

| Sodium urate solutions | Creatinine solutions |
|---|---|
| A = 220 μgl$^{-1}$ | A = 270 μgl$^{-1}$ |
| B = 500 μgl$^{-1}$ | B = 615 μgl$^{-1}$ |
| C = 1000 μgl$^{-1}$ | C = 1230 μgl$^{-1}$ |
| D = 100 μgl$^{-1}$ | D = 123 μgl$^{-1}$ |

Trials were also carried out with a wider range of standard solutions and it was found that the results for uric acid were substantially linear within the concentration range 1–10,000 μgl$^{-1}$ with a precision ($2\sigma$) of ±20% at 2 μgl$^{-1}$ ±4% at 40 μgl$^{-1}$, and ±2% at 10,000 μgl$^{-1}$. For very low concentrations ($\leq 10$ μgl$^{-1}$) results could be confirmed by injections of 1000 μl instead of the usual 100 μl, the analysis times being extended.

Results of analyses of samples taken from environmental waters close to discharges of untreated sewage and sewage after primary and secondary treatments are shown below:

| Typical concentrations of uric acid in Tamar River Catchment sewage discharges | |
|---|---|
| Type of sewage discharge | Uric acid concentration (μgl$^{-1}$) |
| Untreated | 2600,1590,796,490,450 |
| Primary treatment | 2750,680,613,597,590 |
| Secondary treatment (+storm overflow) | $^+$350,$^+$290,<1,<1,<1,<1 |

It was also noted that samples taken close to sewage discharges but outside the sewage plume contained very low concentrations of uric acid.

The results show the sensitivity of the method to uric acid in solutions containing wide varieties and concentrations of other substances and the applicability of the method to the detection of sewage pollution by uric acid determinations.

Tests were also carried out to separate other compounds, such as hippuric acid and creatine, from sewage-containing solutions and to determine their concentrations, with similar success. This offers the possibility of determining information on sources of pollution: for example, sewage from human waste contains a very much smaller proportion of hippuric acid than uric acid whereas secretions from farm animal livestock contain no uric acid but relatively large quantities of hippuric acid. Measurements of the relative concentrations of uric acid and hippuric acid in a sewage sample will thus give information on the relative proportions of the sewage arising from different sources. Such information will not be very precise since the sewage will normally arise from numerous different sources but may be of help, for example, in detecting and tracing pollution in streams resulting directly from livestock on adjacent fields or farms.

A particular advantage of the present method in such studies is that it can be carried out extremely quickly (in a matter of minutes), with small samples and with apparatus which is readily transportable (for example in a Land-Rover) so that it lends itself to use in field experiments.

Uric acid and other determinations were also carried out on sewage treatment plants of the type described below.

Sewage Treatment Plants

Figure 3:
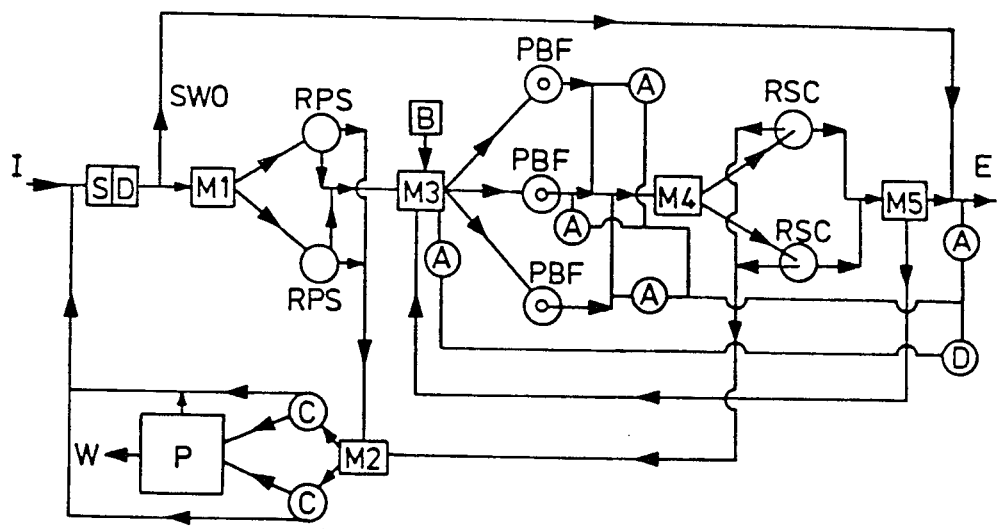
FIG. 3 is a flow diagram illustrating the operation of a percolating-biological-filter sewage-treatment plant.
Figure 4:
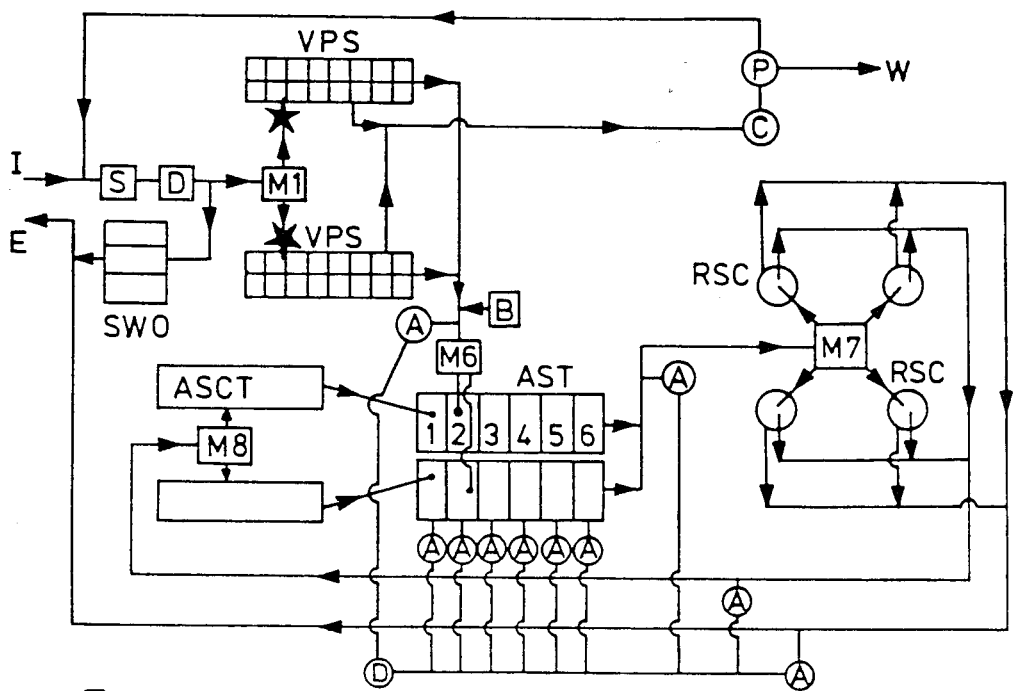
FIG. 4 is a flow diagram illustrating the operation of an activated-sludge sewage-treatment plant.

Reference is now made to FIGS. 3 and 4 of the drawings which are flow diagrams of a percolating biological filter plant and an activated sludge plant respectively both of known type, for processing sewage: the parts and operation of the plants will not be described in detail but, in outline, are as follows:

With reference to FIG. 3, sewage is fed into the percolating biological filter plant at I and passes through screens S and degritters D to a manifold M1. An overflow SWO opens from the duct between the degritters D and the manifold M1 to carry excess storm water. The manifold M1 distributes the sewage to radial flow primary settlers RPS which effect primary separation of suspended solids which are removed as sludge and taken via a manifold M2 to sludge conditioners C and a sludge press P to be discharged at W; liquid from the conditioners C and the press P is recycled to the screens S.

Liquid sewage leaving the primary settlers RPS is distributed via a manifold M3 and sprinkler arms (not shown) to percolating biological filters PBF. Here biological degradation of the fluid takes place before it is discharged to radial flow secondary clarifiers RSC which cleanse it of suspended matter picked up in the filters. This latter is combined with the sludge in the manifold M2 while part of the cleansed liquid is recycled to the manifold M3, the remainder being discharged from the plant at E.

With reference to FIG. 4, the influent sewage at I is again passed through screens S and degritters D to a manifold M1, storm water being drawn off through an overflow SWO. The manifold M1 in this case feeds equal flows to the centers of each of a plurality of vertical-flow primary settlement tanks VPS which effect primary separation of suspended particles; these latter are drawn off as sludge to sludge conditioners C. After pressing in sludge presses P, the sludge is discharged at W and liquid is recycled to the settlement S.

Liquid sewage leaving the settlement tanks VPS is combined and distributed from a manifold M6 to the second tank of each of two series of activated sludge tanks AST, operated independently and in parallel. The liquid sewage passes through the tanks AST in sequence and undergoes biodegradation before being withdrawn from the sixth tank to be fed by a further manifold M7 to radial-flow secondary clarifiers RSC. These latter separate activated sludge from cleansed effluent, the former being recycled via a manifold M8 and sludge conditioning tanks ASCT to the activated sludge tanks AST, and the cleansed effluent being discharged from the plant at E. Various studies were carried out on the plants of FIGS. 3 and 4 involving concentration measurements on constituents of the sewage and investigation of fluid flow paths.

Sewage degradation

In order to assess the efficiency of operation of the sewage treatment plants of FIGS. 3 and 4, concentrations of uric acid, creatinine and other biodegradable compounds dissolved in the flows at various points in the respective systems were measured and the measurements were compared with BOD (Biological Oxygen Demand) and COD (Chemical Oxygen Demand) assessments on samples taken at the same points. The sampling points were as follows:

| Detection points for Activated Sludge Plant (FIG. 4) | | Detection points for Biological Filter plant (FIG. 3) | |
| --- | --- | --- | --- |
| I | Inlet I | I | Inlet I |
| P.S. | Outlet from VPS | P.S. | Outlet from RPS |
| A.S. | Outlet from AST | BF | Outlet from PBF |
| E | Effluent outlet E | E | Effluent outlet E |

The BOD and COD assessments were carried out by the usual known methods and the results are shown graphically in FIGS. 5 to 8, the BOD measurements for the plants of FIGS. 3 and 4 being given in FIGS. 5 and 7 respectively and the COD measurements in FIGS. 6 and 8 respectively: at each site assessments were carried out on three unfiltered samples, taken at half-hour intervals, to give total BOD and COD values (shown by full points with the averages linked by unbroken lines in the drawings) and on the samples after filtration to give dissolved BOD and COD values, (shown by open points with the averages linked by broken lines).

The observed decreases in BOD and COD levels throughout the plants are typical of secondary sewage treatment works in general.

Uric acid and creatinine estimations were carried out on filtered portions of the same samples used for the BOD and COD determinations by the HPLC method described above. The results are shown graphically in FIGS. 9 and 12, the concentrations being given in $\mu gl^{-1}$ on the ordinate against the collection points on the abscissa: FIGS. 9 and 10 show the results for uric acid and creatinine respectively for the biological filter plant of FIG. 3 while FIGS. 10 and 11 show the results for uric acid and creatinine respectively for the activated sludge plant of FIG. 4.

It will be seen from the graphs of FIGS. 9 and 10 that the uric acid and creatinine concentrations fall sharply during passage of the sewage flow through the screens S, degritters D and radial primary settlers RPS of the biological filter plant of FIG. 3; there is a lesser fall in concentration in the biological filters, very little of the dissolved components remaining in the flow after biological degradation therein, and there is practically no reduction in concentration in the secondary clarifiers RSC.

In the activated sludge plant of FIG. 4, the concentration of the creatinine and uric acid in the sewage is not effectively reduced (see FIGS. 10 and 11) in the screens S, degritters D and vertical-flow primary settlers VPS, but the concentrations are reduced substantially in the activated sludge tanks VPS to the very low values allowable in the effluent discharged from the secondary clarifiers RSC. A comparison of FIGS. 5 to 8 and 9 to 12 thus shows marked differences between the BOD/COD changes and uric acid/creatinine changes during primary sedimentation but, other factors also being taken into account, the relative concentration changes in the biodegradation and secondary filter stages in both plants are comparable and, indeed, similar trends were noted for other polar organic dissolved compounds in the sewage i.e. creatine, hippuric acid and tyrosine, which were assayed in other trials.

In particular, the detection of low levels of uric acid (or creatine or other dissolved biodegradable compound) at the outlet from the biodegradation stage or in the effluent E in the plants of FIGS. 3 and 4 were shown to be indicative of low COD and BOD levels at these points and is usable as a rapid alternative to these conventional measurements to check that the plant is operating effectively to reduce pollution in the effluent below statutory levels.

Further studies on the biological filter plant of FIG. 3 showed that the uric acid/creatinine concentration reductions in the screens S, degritters D and primary settlers RPS were due largely to the mixing of primary and secondary clarified waters from the sludge presses P and radial secondary clarifiers RSC respectively at the inlet to the screens S: no actual loss of uric acid or creatinine occurred during primary settlement. In the activated sludge plant only primary clarified water is added to the influent to the screens S, causing very little reduction in the sewage concentration; again no loss of uric acid or creatinine occurred during primary settlement.

In both plants, uric acid, creatinine, and other dissolved organic compounds were found to be removed by biodegradation in the biological filters PBF or activated sludge tanks AST. The concentration reductions in the biodegradation stages were also influenced by the dilution of the sewage which occurred as a result of the input of activated sludge to tank 1 of the activated sludge tanks AST (FIG. 4) and the recycle from the secondary clarifiers RSC (FIG. 3) to the biological filters PBF. Measured concentrations of uric acid or creatinine at points within the biodegradation stage do not therefore represent the proportion of these compounds which have reacted at these points. In order to assess the actual proportion of these compounds which have been degraded, and hence the progress of the overall biodegradation of the liquid sewage, it is necessary to adjust the measurements for dilution.

Tests carried out with bromophenol blue as a tracer, described below, demonstrate that it is usable to give an accurate measurement of fluid flow dilution in the plants of FIGS. 3 and 4.

Bromophenol blue suitability study

Bromphenol blue was screened by simple adsorption tests to examine its suitability as a tracer in highly turbid waters. Standard aqueous solutions of bromophenol blue were prepared which gave an absorbance reading of 0.5 a.u.f.s. at the wavelength of maximum visible absorbance (590) nm). Aliquots (100 ml) of bromophenol blue solutions were in turn shaken with a selection of clays (5 g of either kaolinite, montmorillonite or illite) for 2 hours. An aliquot (10 ml) of each sample was filtered (Whatman GF/F 0.7 μml) and the absorbance measured. Other aliquots of bromophenol blue solution were shaken for one week with garden soil, peat and dewatered sewage sludge (5 g (wet weight) per 100 ml respectively) and absorbance of visible radiation at maximum absorbance (590 nm) recorded for a filtered aliquot (10 ml) of the supernatent liquid. Even under these extreme conditions the bromophenol blue was neither adsorbed nor biodegraded (<10% decolored) by the clays, soil, peat and sewage sludge over the periods studied, at room temperature.

Spectroscopic Analysis of Bromophenol Blue

Samples of sewage (10 ml) containing Bromophenol Blue were collected and filtered, to prevent light scatter during analysis, using Millipore Swinnex (0.25 cm) apparatus fitted with Whatman GF/F filters. The samples were subjected to spectroscopic analysis in a Perkin-elmer Model 552 visible spectrophotometer, fitted with quartz cells (1 cm), each sample being scanned between wavelengths 680 nm and 540 nm. Results of scans on samples containing 50 $gl^{-1}$(A), 100 $gl^{-1}$(B) and 200 $gl^{-1}$(C) of bromophenol blue are shown in FIG. 3 from which it will be seen that bromophenol blue displays an absorption peak at about 590 nm.

The actual bromophenol blue absorbance was calculated by subtracting the value at an extrapolated baseline at 590 nm from the absorbance value (FIG. 1). An absorbance of 0.02 a.u.f.s. was used for maximum sensitivity.

Bromophenol blue concentrations were determined by comparison of absorbances with a standard calibration graph. Response was found to be substantially directly proportional (linear) to concentration within the concentration range 20–10,000 $\mu gl^{-1}$ Precisions of ±10% at a concentration of 20 $\mu gl^{-1}$, 5% at 100 $\mu gl^{-1}$ and 1% at 10,000 $\mu gl^{-1}$, respectively, were recorded for a variety of analyses of Bromophenol blue involving sewage, river and saline water.

Use of bromophenol blue in investigating fluid flows in the plants of FIGS. 3 and 4

(a) Biological filter plant of FIG. 3

190 g of bromophenol blue was added to the liquid flow just before the distribution manifold M3 and its appearance at the sprinkler arms was looked for by visual inspection: it occurred 27 minutes later. Bromophenol blue was also found to take 6 minutes to pass through the biological filter beds PFB.

Samples were also taken at regular intervals from the central core of one of the filter units PBF after biological filtration and from the effluent leaving the secondary clarifier RSC. Spectroscopic analysis of the samples as described above and comparison with the standard calibration curve gave concentration values for the samples which are shown graphically in FIG. 17: curve A shows the values at the filter core while curve E shows the values after clarification.

Assuming an average flow of 38 l $sec^{-1}$ (this sewage works is fed by a series of pumping stations thus there is considerable pulsing of the inlet flow) integration of the mass flow of bromophenol blue with time and volume of flow, indicated that 85% of the added Bromophenol Blue could be accounted for at the filter core within the 3.5 h study period. Integration of the Curve B in FIG. 17 shows that 72% of Bromophenol Blue could be accounted for in the effluent from the clarifiers but sampling was discontinued before all the dye had eluted.

For the duration of the above experiment no effluent was recycled to the biological filters in order to facilitate interpretation of the results.

Times for passage through the various parts of the system may be recorded in a similar manner. If these are recorded while the system is known to be operating efficiently subsequent flow times may be compared with the records to check for abnormalities, such as blockages in the system.

(b) Activated sludge plant of FIG. 4

10 l of water containing a known amount (approx. 200 g) of dissolved bromophenol blue were added to the sewage influent to the primary settlement tanks VPS over a period of 1 minute. Samples were taken at regular intervals at the outlet from the tanks VPS by an automatic sampler and tested for the presence of bromophenol blue by spectroscopic analysis as described above. Results of estimations of the bromophenol blue concentration in the samples are shown graphically in FIG. 14, the concentration being given in $\mu gl^{-1}$ on the ordinate against the time in hours on the abscissa.

The results given in FIG. 14 showed that most of the bromophenol blue had passed through the primary settlement tanks VPS in about 2 hours whereas the system was designed to have an average retention time of the sewage in these tanks of several hours; a restriction causing partial by-pass of the tanks was suspected.

The manifold M1 was cleaned and the test repeated, 210 g of bromophenol blue being introduced: the results are shown in FIG. 15 from which it will be seen that the retention time had increased to about 5 hours, proving the accuracy of the assumption and the utility of the bromophenol blue test.

It should be noted that the blockage was not apparent from visual inspection of the tanks nor from performance tests carried out on the final effluent by C.O.D./B.O.D. analyses.

The results of the second test (FIG. 15) on the sewage works of FIG. 4 were used to check that no significant loss of bromophenol blue occurred during its passage through the settlement tanks.

An average flow rate of 220 l $sec^{-1}$ through the tanks was assumed and the area under the curve of FIG. 15 was integrated. The result showed that 98% of the bromophenol blue could be accounted for.

The above tests confirmed that bromophenol blue is usable in quantitative flow studies in sewage treatment plants and the visible spectroscopic detection method is, indeed, less prone to aberrations than the fluorescence techniques used for other colored tracers, yet it exhibits good sensitivity (20 $\mu g^{-1}$). It may also be mentioned that the lack of dye loss during this study when combined with the above sensitivity makes the use of bromophenol blue cost effective i.e. 36 sterling to define the flow characteristics of a sewage works treating effluent of approximately 63,000 persons (at current dye price of 180 sterling $Kg^{-1}$-plant of FIG. 3). As bromophenol blue does not adsorb onto most solids it would also be suitable for tracer studies in other turbid water environments such as china clay polluted streams, turbid estuaries and hydrological studies in general.

Assessment of flow characteristics of the activated sludge tanks of the plant of FIG. 4

230 g of bromophenol blue was added to the liquid sewage influent to the second tank of one series of activated sludge tanks AST. Samples were taken from each of the six tanks of the series and from the effluent from the secondary clarifiers RSC at regular intervals with a polypropylene bucket. Each sample was examined spectroscopically as described above and its bromophenol blue concentration was calculated.

The results are shown grapically in FIG. 16, the concentrations being given in $\mu gl^{-1}$ on the ordinate against the time from the addition (gulp injection) of bromophenol blue on the abscissa. The results indicate that bromophenol blue mixes rapidly in the system and may enter tank 1 against the flow of activated sludge. Examination of the profiles (FIG. 16) of bromophenol blue concentrations with time in successive tanks indicates increasing mixing and deviation from plug flow, despite the fact that the tanks are separated from each other by baffles designed to minimize inter-tank mixing and to promote plug flow (from tanks 1-6 in order).

Integration of bromophenol blue mass flow with time for tanks 2 and 6 and for the effluent from secondary clarifiers, assuming an average flow of 230 1 sec$^{-1}$ (230±35 1 sec$^{-1}$), indicates that 103% of the bromophenol blue could be accounted for in tank 2 and 95% in the final tank 6, whereas 70% of the bromophenol blue could be accounted for in the final effluent. The low yield for this site may be accounted for by the return of settled sludge to the sludge conditioning tank C (yield calculated allowing for reduced evening sewage flow).

The anomolous figure of "103%" bromophenol blue, given above, is explained by the inaccuracy of the flow rate measurement on this system, determined by current monitoring apparatus. The accuracy of bromophenol blue determinations now having been established, future flow rates may be estimated by bromophenol blue dilution tests.

In particular, bromophenol blue estimations may be used in conjunction with estimations of a biodegradable component of the sewage, such as uric acid, and, in order to facilitate such measurements, the bromophenol blue concentrations are preferably also determined by the HPLC method described above.

Chromatographic analysis of bromophenol blue (FIG. 18)

Four filtered sewage samples containing different, known concentrations of bromophenol blue were analyzed by injecting respective 100 μl aliquots successively on to a Hypersil 5 μm octadecylsilane column (100×4.6 mm, reverse phase) operated with an elution system of 46% v/v methanol, 54% v/v 0.01M sodium dihydrogen orthophosphate, 0.01M disodium hydrogen orthophosphate titrated to pH 7.5, and a flow rate of 2 ml min$^{-1}$ and a pressure of 1,860 psi.

The eluted bromophenol blue was detected with a u.v. variable wavelength detector operated at a wavelength of 570 nm and a sensitivity of 0.005 f.s.d. the results being recorded by a chart run at 1 cm min$^{-1}$; the results are shown in FIG. 18, the peaks A, B and C corresponding to bromophenol blue concentrations of 72 $\mu gl^{-1}$, 150 $\mu gl^{-1}$, 300 $\mu gl^{-1}$ respectively.

The above results provide calibration standards with which results taken from solutions with unknown concentrations are compared to determine their concentrations.

A particular advantage obtained by the use of chromatography prior to spectroscopic analysis will be seen from a comparison of FIGS. 13 and 18. It will be seen that the spectrum of FIG. 13 has a sloping baseline X, determined by extrapolation of the lower, right hand portion of the trace, which leads to inaccuracy in the measurement of the absoption peak due to the bromophenol blue. The spectrum of FIG. 18, however, has a substantially horizontal baseline, allowing more accurate measurement and greater sensitivity.

The differences in the two Figures are due to the fact that the spectrum of FIG. 13 is taken against the background spectrum from sewage in the sample tested, whereas, for FIG. 18, the bromophenol blue has been separated from the sewage by elution and only its own spectrum is seen.

In addition to the increased sensitivity achieved by the chromatographic method there are various other advantages:

The bromophenol blue may be detected by the same apparatus as that used to detect the uric acid, or other organic compound, only the elution system and u.v. filter being changed, thus simplifying the testing of a sewage sample and reducing the cost of apparatus required.

Extremely small samples are required which reduces the sampling, filtering and detection time so that comparative results for bromophenol blue and the organic compound are available within minutes of sampling. In sewage works, in particular, the time reduction achieved compared with previous methods is considerable since samples, of the order of liters, required for B.O.D./C.O.D. measurements took several hours to filter before other tests could be started.

Since the bromophenol blue is removed from all other constituents of a sample, it can be detected uniquely in samples containing compounds with which it might be confused, or which might cause errors in the concentration measurement if the concentration determination were carried on the sample as a whole; for example another compound might be present having an absorption peak at or close to 590 n.m.

It will be appreciated that once the bromophenol blue, uric acid or other selected compound has been separated from a sample by chromatography, it may be analyzed by any suitably selective and sensitive method, such as an electrochemical method, rather than by spectroscopy.

As mentioned above in relation to sewage degradation, the results of measurements on bromophenol blue can be used together with uric acid concentration measurements to determine the progress of the biodegradation reactions in the secondary treatment stages of the plants of FIGS. 3 and 4. For this purpose bromophenol blue is metered into the plants prior to the degradation stage, preferably by automatic metering apparatus B, and samples of the flow are taken at the inlet and at the outlet and, optionally, also from each tank in the biodegradation stage of the plant of FIG. 4. The samples are preferably taken and analyzed automatically for their uric acid and bromophenol blue concentrations by auto-samplers and analyzers A. The results from all the apparatus A may then be fed to a comparator D which effects the necessry comparisons and/or calculations to determine the proportion of uric acid at the inlet to the stage which has been degraded in each subsequent sample. This information may be checked by plant personnel and used to regulate the plant operation. Alternatively, or in addition, the comparator means may be part of a computer arranged to give warnings of malfunctions in the plant or to control the operation of the plant directly to maximise its efficiency.

The bromophenol blue may be metered into the flow continuously or intermittently, the sampling being coordinated with the addition of the tracer. This latter method would suffice in most plants since sewage flows in any one plant do not change rapidly, or indeed to any great extent at all, so that a profile of a plant may be built up with a few test runs and used for comparison with subsequent tests.

What is claimed is:

1. A method of monitoring operational efficiency of a sewage treatment plant having a biodegradation stage, including the steps of:
    sampling flow of sewage at least after outlet from said biodegradation stage;
    filtering each sample taken;
    selecting a single soluble biodegradable compound in the sewage for analysis;
    analyzing respective filtered samples to obtain information relating to the concentration of said selected single biodegradable compound therein; and
    further determining the effectiveness of the biodegradation stage in reducing the concentration to a desired value of all biodegradable compounds in the sewage based upon the information relating to said selected single biodegradable compound.

2. A method as claimed in claim 1, wherein a portion of each filtered sample is eluted by high performance liquid chromatography with an eluent system capable of eluting said selected single biodegradable compound therefrom, and the analysis is effected on the eluent containing said compound.

3. A method as claimed in claim 1, wherein said selected single biodegradable compound is a constituent of the sewage treated in said plant.

4. A method as claimed in claim 3, wherein said single biodegradable compound is selected from uric acid, hippuric acid and creatinine.

5. A method as claimed in claim 1, wherein said flow is also sampled prior to its inlet to said biodegradation stage and at at least one point within said biodegradation stage.

6. A method as claimed in claim 5, wherein the sampling of said flow is carried out automatically at predetermined time intervals.

7. A method as claimed in claim 1, wherein the analysis is effected by a spectrophotometric method.

8. A method as claimed in claim 5, wherein it further includes the steps of:
    adding a measured quantity of a tracer which is inert to the reaction conditions in the biodegradation stage and which is not adsorbed by solid matter in said stage to said flow prior to said inlet to biodegradation stage;
    determining information relative to the concentration of said tracer in each said sample taken; and
    determining, from said information relative to the concentration of said tracer in each said sample together with information relative to the concentration of said selected single biodegradable compound in each said sample, information relating to the proportion of said selected single biodegradable compound in the flow at the inlet to the biodegradation stage which has been biodegraded at said at least one point within said biodegradation stage and at the outlet from said biodegradation stage.

9. A method as claimed in claim 8, wherein the information relative to the concentration of said tracer in each said sample taken is determined by eluting a portion of each said sample by high performance liquid chromatography with an elution system capable of separating said tracer therefrom and analysing the eluent from each sample portion containing said tracer.

10. A method as claimed in claim 9, wherein the analysis for said tracer is effected by a spectrophotometric method.

11. A method as claimed in claim 8, wherein said tracer is bromophenol blue.

12. A method of determining the animal source of sewage effluent in a water body, including the steps of:
    sampling said water body;
    filtering the sample taken;
    eluting respective portions of the filtered sample by high performance liquid chromatography, to separate from said respective portions sewage components of uric acid, hippuric acid and creatinine;
    testing each eluent after chromatography for the presence of a respective component and determining the concentration of said respective component in said sample portions;
    correlating the presence and concentration of said respective components of said sample portions to obtain a correlated value, and then
    comparing said correlated value to a standard value thereby to determine the animal source of said sewage effluent.

13. A method as in claim 12, wherein the determined concentration of said component in said sample is within a range of 1 to 10,000 $\mu$g per liter.

14. A method as in claim 12, wherein said high performance liquid chromatography is performed on an aliquot of from 10 to 1000 $\mu$l of said filtered sample.

15. A method as in claim 12, wherein said testing and determining step includes a spectrophotometric method.

16. In a sewage-treatment plant,
    a monitoring system for a biodegradation stage, said monitoring system comprising
    means for metering a tracer which is inert to reaction conditions in said biodegradation stage and which is not absorbed by solid matter in said stage into the sewage influent to the biodegradation stage;
    respective automatic sampling means for sampling the sewage flow at respective sampling points comprising at least the inlet to and the outlet from said biodegradation stage; and
    analyzer means for effecting plural determinations on each of the samples taken by said respective automatic sampling means, one of said plural determinations being related to the concentration of a single selected, soluble biodegradable sewage component in said sample, and another of said plural determinations being related to the concentration of said tracer in said sample, said analyzer means for generating first and second determination signals representative of said one and another determinations; and comparator means for receiving the processing said first and second determination signals to provide an indication of the operating efficiency of the biodegradation stage whereby the biodegradation stage is monitored.

17. In a sewage-treatment plant, a monitoring system as in claim 16, wherein each said analyzer means includes a high performance liquid chromatograph arranged to separate said selected single biodegradable sewage component and said tracer from said sample in respective elution systems.

18. In a sewage treatment plant, a monitoring system as in claim 17, wherein each said analyzer means further include a spectrophotometer arranged to analyzer said elution systems for the presence of said selected single biodegradable sewage component and said tracer respectively.

19. In a sewage treatment plant, a monitoring system as in claim 16, further including comparator means arranged to receive all said determinations effected by said analyzer means and to process them to provide an indication of the operating efficiency of the degradation stage.

20. A method of monitoring a reaction in a continuous flow system including the steps of:
simultaneously sampling a fluid flow containing a reactant and a tracer inert to reaction conditions at an inlet to a reaction zone and at least one point selected from points within said reaction zone and a point at an outlet from said zone;
subjecting two portions of each sample taken to high performance liquid chromatography, one of said two portions being eluted with an elution system capable of separating said reactant therefrom, and the other of said portions being eluted with an elution system capable of separating said tracer therefrom;
analyzing said elution systems after said chromatography step to determine the concentration of said reactant and said tracer in each said sample; and
determining from said information the proportion of said reactant entering said reaction zone which has reacted at said at least one point.

* * * * *